(12) United States Patent
Boesen

(10) Patent No.: US 10,040,423 B2
(45) Date of Patent: Aug. 7, 2018

(54) VEHICLE WITH WEARABLE FOR IDENTIFYING ONE OR MORE VEHICLE OCCUPANTS

(71) Applicant: BRAGI GmbH, München (DE)

(72) Inventor: Peter Vincent Boesen, München (DE)

( * ) Notice: Subject to any disclaimer, the term of this patent is extended or adjusted under 35 U.S.C. 154(b) by 0 days.

(21) Appl. No.: 15/356,839

(22) Filed: Nov. 21, 2016

(65) Prior Publication Data

US 2017/0151930 A1    Jun. 1, 2017

Related U.S. Application Data

(60) Provisional application No. 62/260,436, filed on Nov. 27, 2015.

(51) Int. Cl.
| | | |
|---|---|---|
| *B60R 25/00* | (2013.01) | |
| *B60R 25/25* | (2013.01) | |
| *H04W 88/02* | (2009.01) | |
| *H04B 1/3827* | (2015.01) | |
| *G07C 9/00* | (2006.01) | |

(52) U.S. Cl.
CPC ........ *B60R 25/257* (2013.01); *G07C 9/00563* (2013.01); *G07C 9/00896* (2013.01); *H04B 1/385* (2013.01); *H04W 88/02* (2013.01)

(58) Field of Classification Search
CPC .............. B60R 25/257; G07C 9/00563; G07C 9/00896; H04B 1/385; H04W 88/02
USPC ....................................................... 340/5.52
See application file for complete search history.

(56) References Cited

U.S. PATENT DOCUMENTS

| | | |
|---|---|---|
| 3,934,100 A | 1/1976 | Harada |
| 4,150,262 A | 4/1979 | Ono |
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |

(Continued)

FOREIGN PATENT DOCUMENTS

| | | |
|---|---|---|
| CN | 204244472 U | 4/2015 |
| CN | 104837094 A | 8/2015 |

(Continued)

OTHER PUBLICATIONS

International Search Report & Written Opinion, PCT/EP2016/078803 (dated Feb. 24, 2017).

(Continued)

*Primary Examiner* — Edwin Holloway, III
(74) *Attorney, Agent, or Firm* — Goodhue, Coleman & Owens, P.C.

(57) ABSTRACT

A system includes a vehicle, the vehicle comprising a control system and a wireless transceiver operatively connected to the control system. The control system is configured to wirelessly communicate with a wearable device worn by a user using the wireless transceiver. The control system is configured to receive biometric input from one or more sensors of the wearable device to identify an occupant of the vehicle or individual proximate the vehicle. The wearable device may be a wearable earpiece with one or more sensors.

18 Claims, 5 Drawing Sheets

(56) References Cited

U.S. PATENT DOCUMENTS

| | | | |
|---|---|---|---|
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,041,410 A * | 3/2000 | Hsu .................. G06K 9/00013 |
| | | 380/285 |
| 6,048,324 A | 4/2000 | Socci et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,140,939 A * | 10/2000 | Flick ....................... B60R 25/04 |
| | | 340/12.28 |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,275,789 B1 | 8/2001 | Moser et al. |
| 6,339,754 B1 | 1/2002 | Flanagan et al. |
| 6,408,081 B1 | 6/2002 | Boesen |
| D464,039 S | 10/2002 | Boesen |
| 6,470,893 B1 | 10/2002 | Boesen |
| 6,472,978 B1 | 10/2002 | Takagi et al. |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,983,628 B2 | 7/2011 | Boesen |
| 8,108,143 B1 | 1/2012 | Tester |
| 8,140,357 B1 | 3/2012 | Boesen |
| 8,610,585 B1 * | 12/2013 | Kielbasa ................ G08B 21/06 |
| | | 180/271 |
| 8,855,918 B2 | 10/2014 | Ranford et al. |
| 8,994,498 B2 | 3/2015 | Agrafioti et al. |
| 9,037,125 B1 | 5/2015 | Kadous |
| 9,081,944 B2 | 7/2015 | Camacho et al. |
| 9,272,711 B1 | 3/2016 | Sivaraman |
| 9,510,159 B1 | 11/2016 | Cuddihy et al. |
| 9,638,537 B2 | 5/2017 | Abramson et al. |
| 2001/0005197 A1 | 6/2001 | Mishra et al. |
| 2001/0025222 A1 | 9/2001 | Bechtolsheim et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 * | 5/2002 | Boesen ................ H04M 1/6033 |
| | | 381/151 |
| 2002/0076073 A1 | 6/2002 | Taenzer et al. |
| 2002/0118852 A1 | 8/2002 | Boesen |
| 2003/0002705 A1 * | 1/2003 | Boesen ................ H04M 1/6066 |
| | | 381/380 |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0124968 A1 * | 7/2004 | Inada ................... B60R 25/2081 |
| | | 340/5.72 |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0220915 A1 | 10/2006 | Bauer |
| 2008/0146890 A1 * | 6/2008 | LeBoeuf ............... A61B 5/0059 |
| | | 600/300 |
| 2008/0254780 A1 | 10/2008 | Kuhl et al. |
| 2009/0002197 A1 | 1/2009 | Cemper |
| 2009/0003620 A1 | 1/2009 | McKillop et al. |
| 2009/0128286 A1 * | 5/2009 | Vitito ................... H05K 5/0208 |
| | | 340/5.8 |
| 2009/0191920 A1 | 7/2009 | Regen et al. |
| 2009/0238386 A1 | 9/2009 | Usher et al. |
| 2010/0033313 A1 | 2/2010 | Keady et al. |
| 2010/0210212 A1 | 8/2010 | Sato |
| 2011/0090093 A1 | 4/2011 | Grimm et al. |
| 2011/0215921 A1 * | 9/2011 | Ben Ayed ................ G08B 1/08 |
| | | 340/539.11 |
| 2011/0227812 A1 | 9/2011 | Haddick et al. |
| 2013/0090744 A1 | 4/2013 | Tran |
| 2013/0322667 A1 | 12/2013 | Christensen |
| 2013/0329051 A1 | 12/2013 | Boesen |
| 2014/0163771 A1 | 6/2014 | Demeniuk |
| 2014/0185828 A1 | 7/2014 | Helbling |
| 2014/0270227 A1 | 9/2014 | Swanson |
| 2015/0028996 A1 * | 1/2015 | Agrafioti ................ G06F 21/40 |
| | | 340/5.82 |
| 2015/0035685 A1 | 2/2015 | Strickland et al. |
| 2015/0148989 A1 | 5/2015 | Cooper et al. |
| 2015/0243172 A1 | 8/2015 | Eskilson |
| 2015/0379859 A1 | 12/2015 | Nespolo |
| 2016/0001781 A1 | 1/2016 | Fung et al. |
| 2016/0033280 A1 | 2/2016 | Moore et al. |
| 2016/0227009 A1 | 8/2016 | Kim et al. |
| 2017/0061751 A1 | 3/2017 | Loermann et al. |
| 2017/0112671 A1 | 4/2017 | Goldstein |
| 2017/0153114 A1 | 6/2017 | Boesen |
| 2017/0153636 A1 * | 6/2017 | Boesen ................... G05D 1/0016 |

FOREIGN PATENT DOCUMENTS

| | | |
|---|---|---|
| DE | 10253192 A1 | 5/2004 |
| DE | 10334203 A1 | 3/2005 |
| DE | 102010003429 A1 | 10/2011 |

(56) References Cited

FOREIGN PATENT DOCUMENTS

| | | |
|---|---|---|
| DE | 102011118966 A1 | 5/2013 |
| EP | 1017252 A2 | 7/2000 |
| EP | 1469659 A1 | 10/2004 |
| GB | 2074817 | 4/1981 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2014046602 A1 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2017034287 A1 | 3/2017 |

OTHER PUBLICATIONS

Announcing the $3,333,333 Stretch Goal (Feb. 24, 2014).
BRAGI Is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, on Track and Gems Overview (Jun. 24, 2015).
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Last Push Before the Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
International Search Report & Written Opinion, PCT/EP16/78790 (dated Apr. 4, 2017).
International Search Report & Written Opinion, PCT/EP2016/078795 (dated Feb. 23, 2017).
International Search Report & Written Opinion, PCT/EP2016/078796 (dated Feb. 23, 2017).
International Search Report & Written Opinion, PCT/EP2016/078797 (dated Feb. 28, 2017).
International Search Report & Written Opinion, PCT/EP2016/078798 (dated Mar. 10, 2017).
International Search Report & Written Opinion, PCT/EP2016/078799 (dated Mar. 1, 2017).
International Search Report & Written Opinion, PCT/EP2016/078800 (dated Feb. 21, 2017).
International Search Report & Written Opinion, PCT/EP2016/078801 (dated Mar. 1, 2017).
Akkermans, "Acoustic Ear Recognition for Person Identification", Automatic Identification Advanced Technologies, 2005 pp. 219-223.
BMW, "BMW introduces BMW Connected—The personalized digital assistant", "http://bmwblog.com/2016/01/05/bmw-introduces-bmw-connected-the-personalized-digital-assistant", (Jan. 5, 2016).
Hyundai Motor America, "Hyundai Motor Company Introduces A Health + Mobility Concept for Wellness in Mobility", Fountain Valley, Califorrna (2017).

* cited by examiner

VEHICLE WITH WEARABLE FOR IDENTIFYING ONE OR MORE VEHICLE OCCUPANTS

PRIORITY STATEMENT

This application claims priority to U.S. Provisional Patent Application 62/260,436, filed on Nov. 27, 2015, and entitled "Vehicle with wearable for identifying one or more vehicle occupants", hereby incorporated by reference in its entirety.

FIELD OF THE INVENTION

The illustrative embodiments relate to vehicles. More particularly, but not exclusively, the illustrative embodiments relate to a vehicle which integrates with or communicates with a wearable device such as an earpiece or a set of earpieces to identify one or more vehicle occupants.

BACKGROUND

Vehicles may come with various types of electronics packages. These packages may be standard or optional and include electronics associated with communications or entertainment. However, there are various problems and deficiencies with such offerings. What is needed are vehicles with improved electronics options which create, improve, or enhance safety and overall experience of vehicles.

SUMMARY

Therefore, it is a primary object, feature, or advantage of the illustrative embodiments to improve over the state of the art.

It is another object, feature, or advantage of the illustrative embodiments to communicate between vehicle systems and wearable devices.

It is a further object, feature, or advantage of the illustrative embodiments to use wearable devices to increase safety in vehicles.

It is a still further object, feature, or advantage of the illustrative embodiments to allow a user to control one or more functions of a vehicle using one or more wearable devices, such as wireless earpieces.

It is a still further object, feature, or advantage of the illustrative embodiments to allow a vehicle to identify a driver based on the presence of a particular wearable device.

It is a still further object, feature, or advantage of the illustrative embodiments to allow a vehicle to identify one or more passengers of a vehicle based on the presence of particular wearable devices.

Yet another object, feature, or advantage of the illustrative embodiments is to allow a vehicle to obtain biometric information about a driver or passenger using one or more wearable devices.

It is another object, feature, or advantage of the illustrative embodiments to enhance an existing vehicle through addition of a wearable device.

One or more of these and/or other objects, features, or advantages of the illustrative embodiments will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

According to one aspect a system includes a vehicle, the vehicle comprising a control system and a wireless transceiver operatively connected to the control system. The control system is configured to wirelessly communicate with a wearable device worn by a user using the wireless transceiver. The control system is configured to receive biometric input from one or more sensors of the wearable device to identify an occupant of the vehicle or individual proximate the vehicle.

According to another aspect a system includes a vehicle, the vehicle comprising a control system, a first wireless transceiver operatively connected to the control system, and a wearable device for being worn by a user, a second wireless transceiver disposed within the wearable device and configured to wirelessly communicate with the first wireless transceiver. The wearable device includes at least one sensor for obtaining biometric input. The wearable device is configured to identify a wearer of the wearable device using the biometric input and convey an identity of the wearer of the wearable device to the control system.

According to another aspect, a system includes a vehicle, the vehicle comprising a vehicle network with a plurality of devices in operative communication with the vehicle network and a wireless transceiver operatively connected to the vehicle network. The wireless transceiver is configured to wirelessly communicate with a wearable device worn by a user and after the user is identified, convey sensor data from the wearable device over the vehicle network to one or more of the plurality of devices.

According to yet another aspect a method includes obtaining sensor data at a wearable device, determining a user's identity based on the sensor data and if the user has appropriate access rights, communicating data or commands over a vehicle network to perform vehicle functions.

DETAILED DESCRIPTION

Some of the most important factors in selecting a vehicle such as a car may be the technology available to enhance the experience. This may be of particular importance in certain vehicle segments, such as for luxury vehicles. Another important factor in selecting a vehicle may be the available safety features. According to various aspects, the illustrative embodiments allow for wearable devices including earpieces to enhance the experience of vehicles and according to some aspects, the illustrative embodiments allow for wearable devices, such as earpieces to enhance the overall safety of the vehicle. Therefore, it is expected that the technology described herein will make any vehicle so equipped more desirable to customers, more satisfying to customers, and potentially more profitable for the vehicle manufacturer and the presence or absence of such technology may drive buying decisions of the consumer. Similarly, at least some of the various aspects may be added to existing vehicles as after-market accessories to improve the safety, accessibility, or experience of existing vehicles.

Figure 1:
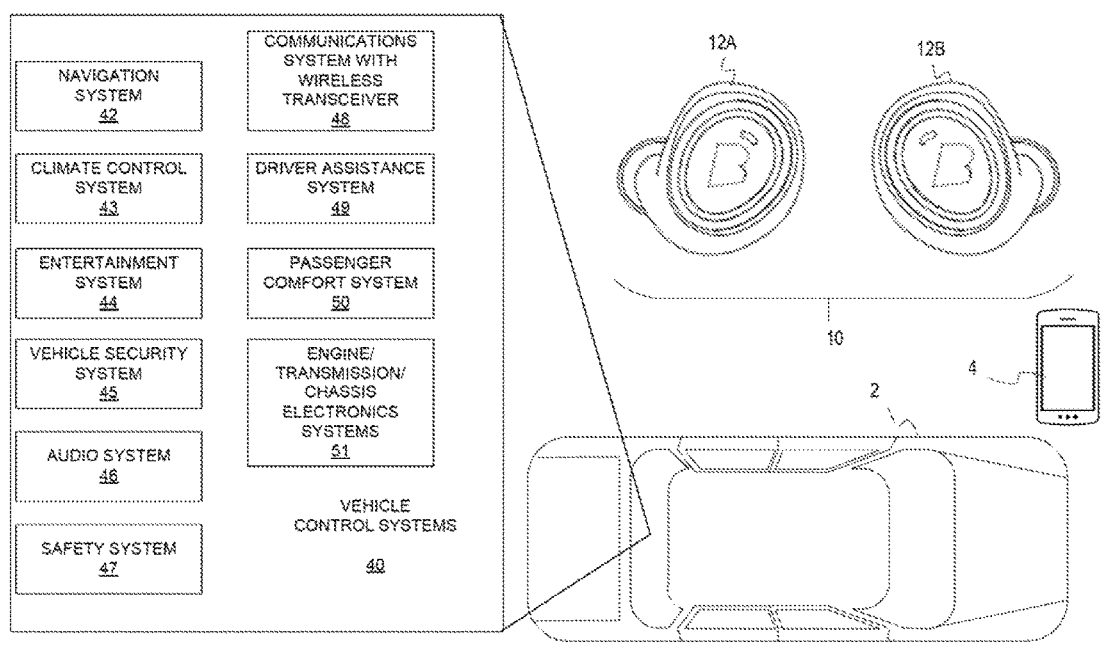
FIG. 1 illustrates one example of a vehicle which integrates with wearable technology.

FIG. 1 illustrates one example of use of a wearable device in conjunction with a vehicle. As shown in FIG. 1 there is a vehicle 2. Although the vehicle 2 shown is a full-size sedan, it is contemplated that the vehicle 2 may be of any number of types of cars, trucks, sport utility vehicles, vans, minivans, automotive vehicles, commercial vehicles, agricultural vehicles, construction vehicles, specialty vehicles, recreational vehicles, buses, motorcycles, aircraft, boats, ships, yachts, trains, spacecraft, or other types of vehicles. The vehicle 2 may be gas-powered, diesel powered, electric, fuel cell, hydrogen, solar-powered, or human-powered. The vehicle 2 may be actively operated by a driver or may be partially or completely autonomous or self-driving. The vehicle 2 may have vehicle control systems 40. The vehicle control systems 40 are systems which may include any number of mechanical and electromechanical subsystems.

As shown in FIG. 1, such systems may include a navigation system 42, an entertainment system 44, a vehicle security system 45, an audio system 46, a safety system 47, a communications system 48 preferably with a wireless transceiver, a driver assistance system 49, a passenger comfort system 50, and engine/transmission/chassis electronics systems 51. Of course, other examples of vehicle control sub-systems are contemplated. In addition, it is to be understood that there may be overlap between some of these different vehicle systems and the presence or absence of these vehicle systems as well as other vehicle systems may depend upon the type of vehicle, the type of fuel or propulsion system, the size of the vehicle, and other factors and variables. All or portions of the vehicle control systems 40 may be integrated together or in separate locations of the vehicle 2.

In the automotive context, examples of the driver assistance system 49 may include one or more subsystems such as a lane assist system, autopilot, a speed assist system, a blind spot detection system, a park assist system, and an adaptive cruise control system. In the automotive context, examples of the passenger comfort system 50 may include one or more subsystems such as automatic climate control, electronic seat adjustment, automatic wipers, automatic headlamps, and automatic cooling. In the automotive context, examples of the safety system 47 may include active safety systems such as air bags, hill descent control, and an emergency brake assist system. Aspects of the navigation system 42, the entertainment system 44, the audio system 46, and the communications system 48 may be combined into an infotainment system.

One or more wearable devices such as a set of earpieces 10 including a left earpiece 12A and a right earpiece 12B may in operative communication with the vehicle control system 40, such as through the communication system 48. For example, the communication system 48 may provide a Bluetooth, Wi-Fi, or BLE link to wearable devices or may otherwise provide for communications with the wearable devices through wireless communications. The vehicle 2 may communicate with the wearable device(s) directly, or alternatively, or in addition, the vehicle 2 may communicate with the wearable device(s) through an intermediary device such as a mobile device 4 which may be a mobile phone, a tablet, gaming device, media device, computing device, or other type of mobile device.

As will be explained in further details with respect to various examples, one or more of the earpieces 10 interact with the vehicle control system 40 in any number of different ways. For example, the earpieces 10 may provide sensor data, identity information, stored information, streamed information, or other types of information to the vehicle. Based on this information, the vehicle may take any number of actions which may include one or more actions taken by the vehicle control system (or subsystems thereof). In addition, the vehicle 2 may communicate sensor data, identity information, stored information, streamed information or other types of information to the earpieces 10.

Figure 2:
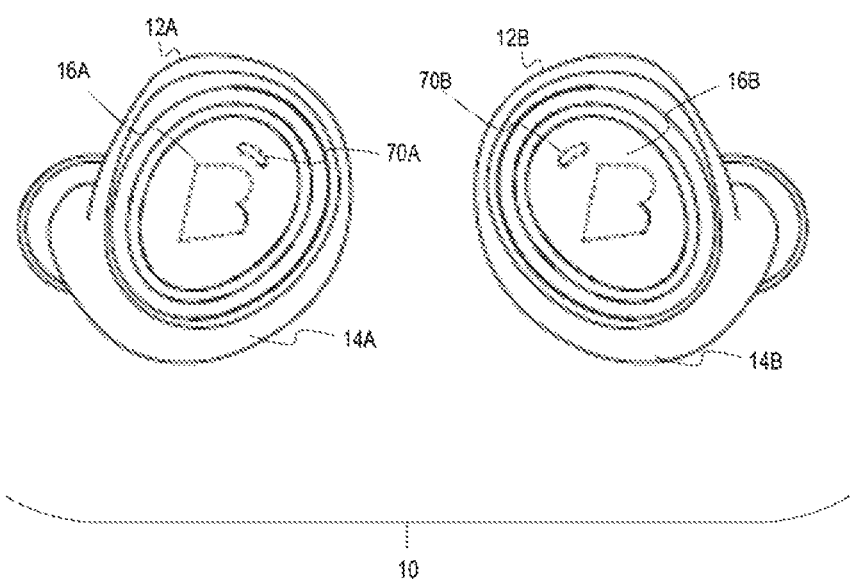
FIG. 2 illustrates one example of a set of wearable devices in the form of earpieces.

FIG. 2 illustrates one example of a wearable device in the form of a set of earpieces 10 in greater detail. FIG. 1 illustrates a set of earpiece wearables 10 which includes a left earpiece 12A and a right earpiece 12B. Each of the earpieces 12A, 12B has an earpiece wearable housing 14A, 14B which may be in the form of a protective shell or casing and may be an in-the-ear earpiece housing. A left infrared through ultraviolet spectrometer 16A and right infrared through ultraviolet spectrometer 16B is also shown. Each earpiece 12A, 12B may include one or more microphones 70A, 70B. Note that the air microphones 70A, 70B are outward facing such that the air microphones 70A, 70B may capture ambient environmental sound. It is to be understood that any number of microphones may be present including air conduction microphones, bone conduction microphones, or other audio sensors.

Figure 3:
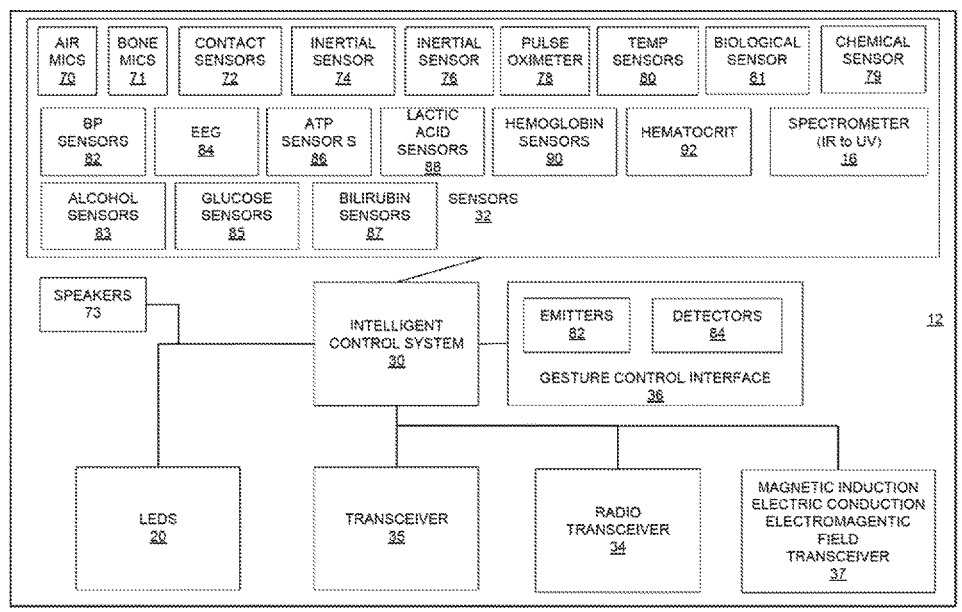
FIG. 3 is a block diagram of one example of a wearable device in the form of an earpiece.

FIG. 3 is a block diagram illustrating an earpiece 12. In other embodiments, the earpieces 12 may represent an over-ear headphone, headband, jewelry, or other wearable device. The earpiece 12 may include one or more LEDs 20 electrically connected to an intelligent control system 30. The intelligent control system 30 may include one or more processors, microcontrollers, application specific integrated circuits, or other types of integrated circuits. The intelligent control system 30 may also be electrically connected to one or more sensors 32. Where the device is an earpiece 12, the sensors 32 may include an inertial sensor 74 and another inertial sensor 76. Each inertial sensor 74, 76 may include an accelerometer, a gyro sensor or gyrometer, a magnetometer, or other type of inertial sensor. The sensors 32 may also include one or more contact sensors 72, one or more bone conduction microphones 71, one or more air conduction microphones 70, one or more chemical sensors 79, a pulse oximeter 76, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the earpieces 12. These may include a blood pressure sensor 82, an electroencephalogram (EEG) 84, an Adenosine Triphosphate (ATP) sensor, a lactic acid sensor 88, a hemoglobin sensor 90, a hematocrit sensor 92, or other biological or chemical sensors.

A spectrometer 16 is also shown. The spectrometer 16 may be an infrared (IR) through ultraviolet (UV) spectrometer although it is contemplated that any number of wavelengths in the infrared, visible, X-ray, gamma ray, radio, or ultraviolet spectrums may be detected. The spectrometer 16 may be adapted to measure environmental wavelengths for analysis and recommendations and thus may be located on or at the external facing side of the earpiece 12.

A gesture control interface 36 is also operatively connected to or integrated into the intelligent control system 30. The gesture control interface 36 may include one or more emitters 82 and one or more detectors 84 for sensing user gestures. The emitters 82 may be one of any number of types including infrared LEDs. The earpiece 12 may include a transceiver 35 which may allow for induction transmissions such as through near field magnetic induction. A short-range transceiver 34 using Bluetooth, BLE, UWB, Wi-Fi or other means of radio communication may also be present. The short range transceiver 34 may be used to communicate with the vehicle control system. In operation, the intelligent control system 30 may be configured to convey different information using one or more of the LED(s) 20 based on context or mode of operation of the device. The various sensors 32, the processor 30, and other electronic components may be located on one or more printed circuit boards, chips, or circuits of the earpiece 12. One or more speakers 73 may also be operatively connected to the intelligent control system 30.

A magnetic induction electric conduction electromagnetic (E/M) field transceiver 37 or other type of electromagnetic field receiver is also operatively connected to the intelligent control system 30 to link the processor 30 to the electromagnetic field of the user. The use of the E/M transceiver 37 allows the earpiece 12 to link electromagnetically into a personal area network or body area network or other device.

According to another aspect, earpiece wearables may be used to identify one or more users. Each earpiece wearable may include its own identifier (e.g., IMEI, RFID tag, unique frequency, serial number, electronic identifier, user-specified name, etc.). In addition, each earpiece 12 may be used to determine or confirm identity of an individual wearing it. This may be accomplished in various ways including through voice imprint. In particular, an individual may speak and their voice may be analyzed by the earpiece 12 and compared to known samples or metrics in order to identify the individual. Fingerprints, gestures, tactile feedback, height, skin conductivity, passwords, or other information may also be determined by the sensors 32 or the earpiece 12 and utilized for authentication.

Other types of user identification and authentication may also be used. For example, an individual may be asked to specify other information to the earpiece 12 in order to confirm identity. This may include answering specific questions. For example, the earpiece 12 may ask multiple questions with yes, no, multiple choice, or free form answers which the correct individual will know but others are not likely to know. These questions may be stored within a database and are questions which the individual associated with the earpiece 12 specifically provided answers for. These questions may also be based on activities of the user which are stored on the earpiece 12 or are retrievable from a system in operative communication with the earpiece 12. These may include information about physical activities, locations, or other activities.

Alternatively, instead of the earpiece performing the analysis associated with user identification and authentication, necessary information, such as voice samples or voice or gestural responses may be collected by the earpiece 12 and communicated to the vehicle, mobile device, or other device for performing the analysis.

Once a user has been identified the user may be authorized to perform various functions in various ways. For example, the vehicle may be unlocked such as by a person saying "unlock" or the vehicle may be remote started and environmental controls set by a person saying "start my car and set temperature to 72 degrees." These actions may be taken by the vehicle control system or its subsystems such as an access and security subsystem or a climate control subsystem. In addition, actions may be taken based on proximity of the individual to the user or based on other contextual information.

Various types of vehicle controls may be a part of the vehicle access and security subsystems. These may include actuators such as actuators associated with door locks or locks associated with other compartments. Other types of vehicle controls may include an ignition lock switch which may be unlocked or locked. Other types of vehicle controls may include actuators associated with windows. In addition to these functions, any number of different vehicle functions or related processes may be performed. The vehicle functions performed by a properly identified individual may be the same types of vehicle functions that an individual may perform as a driver of the vehicle. Other types of vehicle controls may include any number of settings such as audio system settings, engine controls/components, temperature control settings, entertainment system settings, navigation settings, or other types of settings. The earpiece 12 may also be utilized to control (e.g., initiate, end, adjust settings, etc.) vehicle tracking systems, camera systems, anti-locking breaks, traction control systems, four wheel drive systems, electronic stability control (ESC), dynamic steering response, driver wakefulness monitoring, assured clear distance ahead, adaptive headlamps, advanced automatic collision notification, automotive night vision, blind spot monitoring, precrash systems, safe speed governing, traffic sign recognition, dead man's switch, and so forth.

Figure 4:
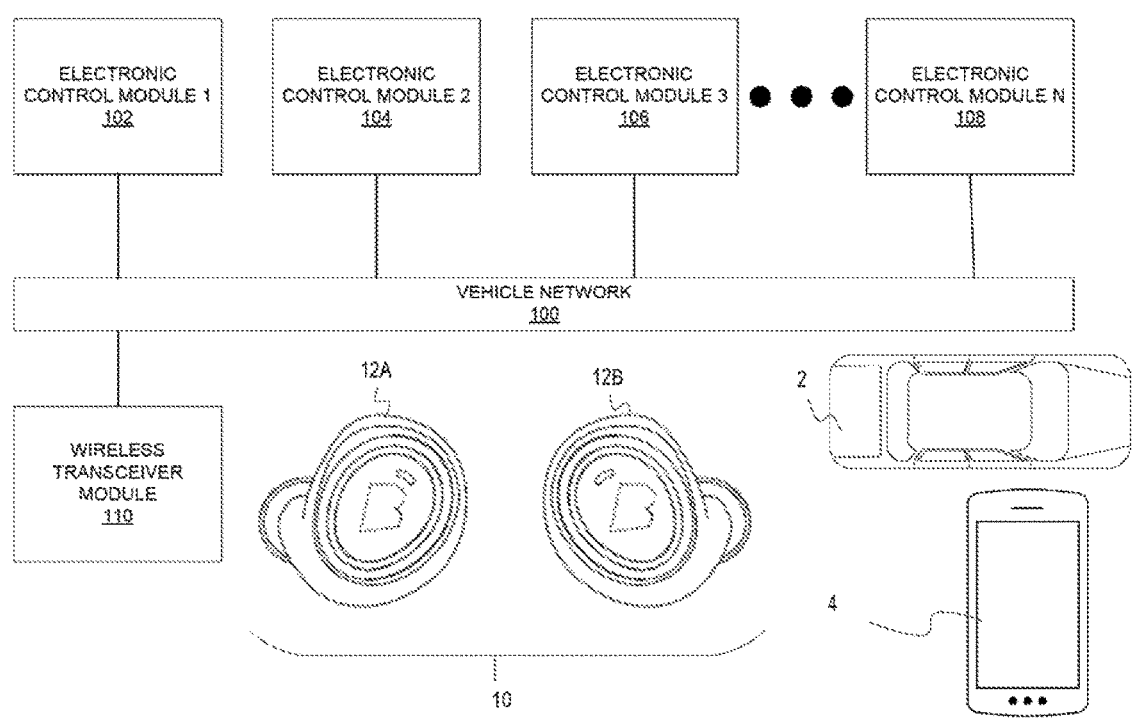
FIG. 4 illustrates a vehicle network or bus allowing different electronic modules to communicate with a wearable device.

FIG. 4 illustrates another example. In FIG. 4, a vehicle network 100 is shown. According to one aspect, the left earpiece and the right earpiece 12A, 12B may communicate information through a vehicle network 100 associated with the vehicle 2. Thus, once an identity of a user has been established, commands may be communicated over the vehicle network 100 or vehicle bus to perform one or more vehicle functions. Protocols which are used may include a Controller Area Network (CAN), Local Interconnect Network (LIN), local area network (LAN), personal area network (PAN), or others including proprietary network protocols or network protocol overlays.

Various types of electronic control modules 102, 104, 106, 108 or electronic control units may communicate over the network 100 of the vehicle 102. These may include electronic modules such as an engine control unit (ECU), a transmission control unit (TCU), an anti-lock braking system (ABS), a body control module (BCM), a door control unit (DCU), an electric power steering control unit (PSCU), a human-machine interface (HMI), powertrain control module (PCM), speed control unit (SCU), telematic control unit (TCU), brake control unit (BCM), battery management system, and numerous others. Any number of electronic control modules may be operatively connected to the vehicle network 100. The commands may represent audio or verbal commands, tactile commands (e.g., taps, swipes, etc.), head gestures, hand motions near the earpieces 12, or other detectable user feedback. In one embodiment, the various commands may be associated with different components and functions of the electronic control modules 102, 104, 106, 108. The earpieces 10, an associated wireless device, an electronic device, or the vehicle 2 interface may be utilized to associate the commands with specific actions. Databases, memory data, macro, or scripts may associate the user command, input, or feedback with the implemented action. For example, an application or set of instructions executed by the vehicle 2 may associate a head gesture, such as two head nods, with an unlock function for the driver's side door of the vehicle 12.

In one embodiment, a wireless transceiver module 110 is operatively connected to a vehicle network 100 and it is the wireless transceiver module 110 which is in operative communication with one or more wearable devices, such as the wearable earpieces 10. Once an earpiece 12A, 12B or the vehicle 2 has identified a user, then that user is permitted to give instructions which are translated into commands which are communicated over the vehicle network 100 to an appropriate system or component of the vehicle or to communicate data such as data from one or more sensors of each of the earpieces 12A, 12B. Data from the earpieces 10 may be used by any number of different electronic control modules or electronic control units 102, 104, 106, 108 connected to the vehicle network 100 to perform any number of different vehicle functions.

Figure 5:
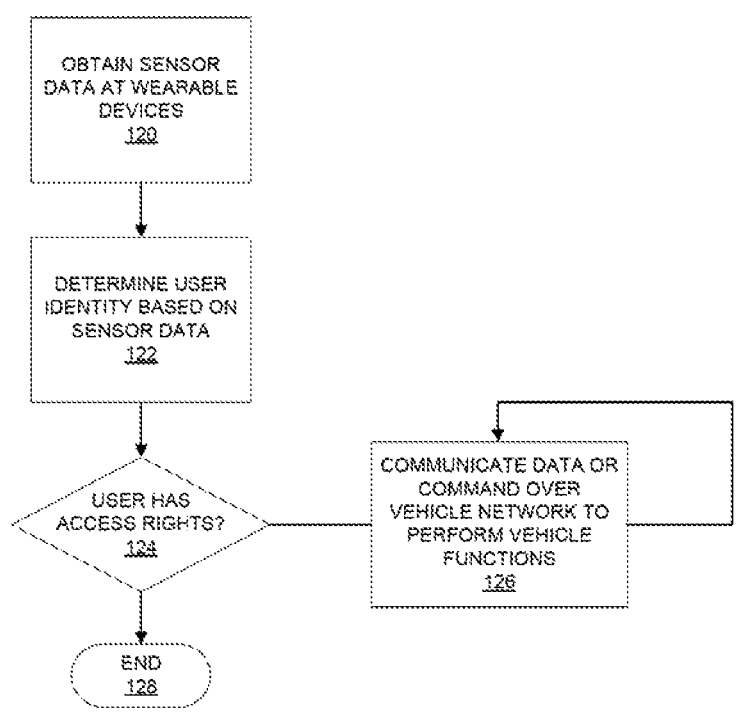
FIG. 5 illustrates one example of a method.

FIG. 5 illustrates one example of a methodology. In one embodiment, the one or more wearable devices may represent one or more wireless earpieces, such as those that are shown and described in the various embodiments. As shown in FIG. 5 at step 120 sensor data is obtained at one or more wearable devices. As previously explained the sensor data may be one of any number of types. For example, the sensor data may be voice data or other biometric data. In step 122 a determination is made of the user identity based on the sensor data. Where the sensor data is voice data this determination may be as the result of a voice print or voice sample analysis. Any number of different products or components may be used to perform this analysis. Examples of commercial products for performing such functionality include Nuance VocalPassword, Watson, Siri, Alexa, Google Voice, VoiceIT, and numerous others. It should be further understood that other types of biometric data may be used. For example, where the wearable device is a pair of glasses than retina identification and authentication may be used. Where the wearable device is a pair of gloves, finger print analysis may be used. Similarly, wireless earpieces may be utilized to scan fingerprints as well. The determination of the user identify based on sensor data may be performed in one of several different locations based on the type of analysis and available computational resources. For example, the determination may be performed on or at the wearable device itself. Alternatively, the determination may be performed on or at the vehicle. Alternatively still, the determination may be performed by a mobile device such as a smart phone which is in operative communication with either the wearable device(s) or the vehicle, or both.

Once the individual has been identified or recognized, in step 124 a determination is made as to whether the user has access rights. In one implementation, if the user is identified then the user has appropriate access rights. In alternative implementations, identifying the user does not necessarily give the individual all rights. Where the user has appropriate access rights or none are required, in step 126 data or commands may be communicated over the vehicle network to perform various vehicle functions. Data from the wearable device(s) may be used by any electronic control modules associated with the vehicle network to provide input to be used in any number of different decision-making processes. Similarly, commands may be given from the user to the vehicle using the wearable device such as when the wearable device is an earpiece and the commands may be given through voice input from the user.

Any number of actions or access may be granted for implementation utilizing one or more of the earpieces, vehicle systems, wireless devices, or other networked devices. In one example, the user may receive a phone call through a wireless device within the vehicle or by a communication system within the vehicle. In response to the user being authorized or authenticated, the user may provide feedback utilizing the wireless earpieces, such as a double head nod, thereby accepting the phone call for communication through the speakers and microphones of the vehicle. In addition, the communications may be communicated through the wireless earpieces and augmented by the vehicle communication systems (e.g., displaying the caller, call length, etc.).

In another example, the user may provide a verbal command, such as "enter sport mode", thereby providing a command to the vehicle to adjust the performance of the vehicle (e.g., engine torque/output, transmission performance, suspension settings, etc.). The wireless earpieces may be configured to listen for or receive a command at any time. In other embodiments, a "listen" mode may be activated in response to an input, such as a finger tap of the wireless earpieces, initiation of a vehicle feature, head motion, or so forth. The listen mode may prepare the wireless earpieces to receive a command, input, or feedback from the user.

In another example, the wireless earpieces may provide a method of monitoring biometrics of the user, such as heart rate, blood pressure, blood oxygenation, respiration rate, head position, voice output, or other measurements or readings detectable by the various sensors within the wireless earpieces and/or the vehicle. For example, the wireless earpieces may determine that the user is fatigued based on the user's heart rate, respiration, and head motion in order to provide an alert through the vehicle systems, such as a message indicating that the user should pull over communicated through the infotainment system, a heads up display (e.g., electronic glass), or other vehicle systems. For example, the user settings may indicate that the windows are rolled down and the music is turned up until the user can find a suitable place to stop or park. The wireless earpieces may also warn the user if he is impaired based on a determined blood alcohol level, cognition test, slurred speech, or other relevant factors. As a result, the wireless earpieces may help protect the user from his or herself, passengers within the vehicle, and third parties that may be outside the vehicle. In one embodiment, the wireless earpieces may be configured to lock out one or more vehicle systems in response to determining the user is impaired.

The wireless earpieces may also indicate biometrics in the event there is an accident, health event, or so forth. For example, the wireless earpieces may send a command for the vehicle to enter an emergency pullover mode in response to determining the user is experiencing a health event, such as a heart attack, stroke, seizure, or other event or condition that prevents the user from safely operating the vehicle. The wireless earpieces may also send one or more communications to emergency services, emergency contacts, or so forth.

In another example, the wireless earpieces may be utilized to monitor a younger or inexperienced user operating the vehicle. For example, to operate the vehicle, an administrator of the vehicle may require that the wireless earpieces be worn to determine the watchfulness of the user determined by factors, such as head position, conversations or audio detected, activation/utilization of and associated cellular phone, the wireless earpieces, or the vehicle systems. As a result, the wireless earpieces may be utilized as a parental monitoring feature wall the user is within the vehicle.

The wireless earpieces may also be utilized to perform any number of small tasks that may significantly enhance the user experience, such as opening individual doors, unlocking the trunk, opening windows/sunroofs, starting the vehicle, turning off the vehicle, turning on or off the air conditioning/heater, adjust a seat configuration, turning on a movie/music, or any number of other features commonly utilized by the user.

The wireless earpieces in conjunction with the vehicle systems, may also learn the preferences of the user over time in order to perform automatic features and settings of the vehicle.

It is further contemplated that particular commands may be automatically communicated based on the identity of the user. In other words, once the user has been identified the vehicle may perform one or more vehicle functions automatically based on the identity of the user. These functions may be any number of different functions previously discussed including functions that grant access or deny access to the user.

Various methods, system, and apparatus have been shown and described relating to vehicles with wearable integration or communication. The present invention is not to be limited to these specific examples but contemplates any number of related methods, system, and apparatus and these examples may vary based on the specific type of vehicle, the specific type of wearable device, and other considerations.

What is claimed is:

1. A system comprising:
   a vehicle, the vehicle comprising a control system; and
   a wireless transceiver operatively connected to the control system;
   wherein the control system is configured to wirelessly communicate with a wireless earpiece worn by a user using the wireless transceiver;
   wherein the control system is configured to receive biometric input from one or more sensors of the wireless earpiece to identify an occupant of the vehicle or an individual proximate to the vehicle;
   wherein the wireless earpiece is configured to confirm identity by providing a question to the occupant of the vehicle or the individual proximate to the vehicle in response to a successful identification of the occupant of the vehicle or the individual proximate to the vehicle by the control system using the biometric input; and
   wherein the control system is further configured to provide access to the vehicle in response to a successful response to the question by the occupant of the vehicle or the individual proximate to the vehicle.

2. The system of claim 1 wherein the access is provided by unlocking an ignition of the vehicle.

3. The system of claim 1 wherein the access is provided by opening a door or compartment of the vehicle.

4. The system of claim 1 wherein the control system is configured to deny access to the vehicle after identifying the occupant of the vehicle or the individual proximate the vehicle.

5. The system of claim 1 wherein the control system is configured to alter one or more vehicle settings based on an identity of the occupant or the individual proximate to the vehicle.

6. The system of claim 1 wherein the one or more sensors comprises a microphone and wherein the biometric input is a voice input.

7. A system comprising:
   a vehicle, the vehicle comprising a control system;
   a first wireless transceiver operatively connected to the control system; and
   a wireless earpiece for being worn by a user, the wireless earpiece including a second wireless transceiver disposed within the wireless earpiece and configured to wirelessly communicate with the first wireless transceiver;
   wherein the wireless earpiece comprises at least one sensor for obtaining biometric input and at least one inertial sensor for detecting motion;
   wherein the wireless earpiece is configured to identify the user of the wireless earpiece using the biometric input and convey an identity of the user of the wireless earpiece to the control system; and
   wherein the wireless earpiece is configured to monitor the user and alert the user if the biometric input independent from the at least one inertial sensor indicates the user is impaired.

8. The system of claim 7 wherein the control system is configured to provide access to the vehicle after identifying the user of the vehicle.

9. The system of claim 8 wherein the access is provided by unlocking an ignition of the vehicle.

10. The system of claim 8 wherein the access is provided by opening a door or compartment of the vehicle.

11. The system of claim 7 wherein the control system is configured to deny access to the vehicle upon a successful identification of the user by the wireless earpiece.

12. The system of claim 7 wherein the control system is configured to alter one or more vehicle settings based on the identity of the user or the individual proximate the vehicle.

13. The system of claim 7 wherein the at least one sensor comprises a microphone and wherein the biometric input is a voice input.

14. A system comprising:
   a vehicle, the vehicle comprising a vehicle network with a plurality of control modules in operative communication with the vehicle network;
   a first wireless transceiver operatively connected to the vehicle network; and
   a wireless earpiece worn by a user and in operative communication with the vehicle network via the first wireless transceiver;
   wherein the wireless earpiece comprises an intelligent control system, a second wireless transceiver operatively connected to the intelligent control system; and
   a plurality of sensors operatively connected to the intelligent control system, wherein the plurality of sensors comprises at least two different types of sensors;
   wherein the plurality of sensors is configured to receive biometric data associated with the user;
   wherein the wireless earpiece is configured to analyze the biometric data from the wireless earpiece to identify the user;
   wherein the wireless earpiece is configured to confirm identity by providing at least one question to the user in response to a successful identification of the user;
   wherein the first wireless transceiver is configured to convey sensor data from the wireless earpiece over the vehicle network to one or more of the plurality of control modules; and
   wherein the plurality of control modules comprises an engine control unit, a transmission control unit, an anti-lock braking system, a door control unit, an electric power steering control unit, a powertrain control module, a speed control unit, and a brake control unit.

15. The system of claim 14 wherein the plurality of control modules are controlled by the wireless earpiece based on user input detected by the wireless earpiece.

16. The system of claim 7 wherein the wireless earpiece is configured to provide at least one question to the user stored on a database of a third party device.

17. The system of claim 14 wherein the at least one question is stored on a database of the vehicle.

18. The system of claim 14 wherein the sensor data includes a head gesture and the vehicle is configured to associate the head gesture with a vehicle function.

\* \* \* \* \*